(12) United States Patent
Sette

(10) Patent No.: US 10,835,211 B2
(45) Date of Patent: Nov. 17, 2020

(54) FLOW SENSOR ARRANGEMENT AND METHOD FOR USING A FLOW SENSOR ARRANGEMENT

(71) Applicant: Medyria AG, Winterthur (CH)

(72) Inventor: Massimo Sette, Solothurn (CH)

(73) Assignee: MEDYRIA AG, Winterthur (CH)

( * ) Notice: Subject to any disclaimer, the term of this patent is extended or adjusted under 35 U.S.C. 154(b) by 567 days.

(21) Appl. No.: 14/893,522

(22) PCT Filed: May 21, 2014

(86) PCT No.: PCT/CH2014/000068
§ 371 (c)(1),
(2) Date: Nov. 23, 2015

(87) PCT Pub. No.: WO2014/186912
PCT Pub. Date: Nov. 27, 2014

(65) Prior Publication Data
US 2016/0113628 A1    Apr. 28, 2016

(30) Foreign Application Priority Data
May 24, 2013   (CH) ...................................... 1010/13

(51) Int. Cl.
*A61B 8/06*     (2006.01)
*A61B 8/08*     (2006.01)
(Continued)

(52) U.S. Cl.
CPC .............. *A61B 8/488* (2013.01); *A61B 5/026* (2013.01); *A61B 5/6853* (2013.01); *A61B 8/06* (2013.01);
(Continued)

(58) Field of Classification Search
CPC ......... A61B 5/026; A61B 5/6853; A61B 8/06; A61B 8/12; A61B 8/488; A61B 8/58; G01F 1/68; G01P 5/12
See application file for complete search history.

(56) References Cited

U.S. PATENT DOCUMENTS 3,595,079 A    7/1971 Grahn
4,152,934 A *  5/1979 Weller ...................... G01P 5/06
                                                        73/170.11
(Continued)

FOREIGN PATENT DOCUMENTS

WO    WO 03086520     10/2003
WO    WO 2004069030   8/2004
(Continued)

OTHER PUBLICATIONS

M. Shikida, et al., "Characteristics of an optimized catheter-type thermal flow sensor for measuring reciprocating airflows in bronchial pathways", Journal of Micromechanics and Microengineering, Nov. 29, 2010, p. 1-11.
(Continued)

*Primary Examiner* — Mark D Remaly
(74) *Attorney, Agent, or Firm* — Straub & Straub; Michael P. Straub; Stephen T. Straub

(57) ABSTRACT

A flow sensor arrangement (S35, S36. S37, S39, . . . ) is located on an elongated body (C1, C2, C3, . . . ) for measuring the flow of a fluid, with one or more flow sensors (S1, S2, S3, . . . ) being arranged on the elongated body (C1, C2, C3, . . . ) to measure the flow along different spatial directions.

18 Claims, 12 Drawing Sheets

(51) Int. Cl.
  *A61B 5/00* (2006.01)
  *G01P 5/12* (2006.01)
  *G01F 1/68* (2006.01)
  *A61B 5/026* (2006.01)
  *A61B 8/12* (2006.01)
  *A61B 8/00* (2006.01)

(52) U.S. Cl.
  CPC ................ *A61B 8/12* (2013.01); *A61B 8/58* (2013.01); *G01F 1/68* (2013.01); *G01P 5/12* (2013.01)

(56) References Cited

U.S. PATENT DOCUMENTS

| | | | |
|---|---|---|---|
| 6,234,004 B1* | 5/2001 | Revsbech | G01F 1/34 73/19.04 |
| 6,503,202 B1* | 1/2003 | Hossack | A61B 8/06 600/454 |
| 2002/0123749 A1 | 9/2002 | Jain | |
| 2004/0031331 A1* | 2/2004 | Blakley | A61M 15/009 73/862.52 |
| 2004/0055374 A1* | 3/2004 | Cohen | G01F 1/684 73/204.11 |
| 2005/0165324 A1 | 7/2005 | Receveur et al. | |
| 2006/0270915 A1 | 11/2006 | Ritter et al. | |
| 2007/0016072 A1 | 1/2007 | Grunwald et al. | |
| 2012/0316419 A1 | 12/2012 | Chevalier | |
| 2012/0318058 A1* | 12/2012 | Kimura | G01F 1/6842 73/204.23 |
| 2014/0012242 A1* | 1/2014 | Lee | A61B 18/18 606/21 |

FOREIGN PATENT DOCUMENTS

| WO | WO 2008002606 | 1/2008 |
|---|---|---|
| WO | WO 2011072186 | 6/2011 |
| WO | WO 2011101813 | 8/2011 |

OTHER PUBLICATIONS

PCT Notification of Transmittal of the International Preliminary Report on Patentability from application PCT/CH2014/000068(1 Page) dated Oct. 2, 2015.

PCT Preliminary Report on Patentability International Application PCT/CH2014/000068 (pp. 1-8) dated Oct. 2, 2015.

International Search Report and Written Opinion of the International Searching Authority from application PCT/CH2014/000068, pp. 1-10 dated Aug. 5, 2014.

* cited by examiner

FLOW SENSOR ARRANGEMENT AND METHOD FOR USING A FLOW SENSOR ARRANGEMENT

There is a class of surgical procedures called interventional procedures or minimal invasive procedures, which foresees the introduction of a catheter within the human vasculature. The catheter is used to deploy a device, make measurements, make treatment or inject a fluid.

In the common procedure the catheter is introduced form an opening in a blood vessel, e.g. in the groin or in the carotids. Through this opening the catheter is then advanced until the region of interest, and there is performed the intervention: deploy a device, make a treatment or measurement or inject fluid.

In general the catheter's position is visualized by means of x-ray based machines, x-rays are ionizing radiations potentially harmful for the patients and the doctors, and this is the reason why there is a constant need and trend to reduce at minimum its use. Moreover the use of x-rays is often coupled with the use of a contrast dye. The contrast dye is an iodinated solution that is injected into the vessel under examination, its use makes possible to enhance some important structures with vessels such as the side branches. The contrast dye is not free from side effect, its use induces sufferance in other organs, e.g. the kidneys, and depending on the patient's pathological status it can lead to permanent kidney impairment.

However the use of both contrast dye and x-ray is necessary because is the only effective way by which the surgeons can visualize important anatomical structures like, vessels, side branches or bifurcations.

WO 2011/072186 A1 describes two pressure sensors placed on a catheter. The catheter is partially introduced into an orifice to occlude a side branch. The pressure drop between the portion of the catheter inside and outside the orifice is used to monitor the correct occlusion of the orifice. Another embodiment discloses integration into the catheter of a flow sensor mounted on a tubular body.

WO 2008/002606 A2 presents an apparatus and method for intra-cardiac mapping and ablation. The application of the device is the mapping of the flow within the atrium (heart), it is used for mapping the position of the pulmonary veins ostia. The device disclosed in this patent is a catheter with a mesh/grid of sensors at its extremity. The sensors are used for mapping the flow through the mesh inside the heart. The sensors sense the blood flow measuring the convective cooling effect of a heated sensor, i.e. it is sensed the resistance change of a heated resistive wire. A constant current is fed into the resistance and the voltage is measured. The temperature of the sensor is about 1 C above the blood temperature. However, the apparatus requires that the flow takes place through the mesh, which is not suited for recognizing a flow distribution along a catheter or along a vessel. Furthermore, constant current anemometry is limited in that it has a low lifetime, low frequency response and influenced by fluctuations of the blood temperature.

US 2006/0270915 A1 describes a catheter for the navigation into the heart, for treating arrhythmia. In one embodiment the catheter senses the blood flow by means of sensor sensing the temperature changes across a region of the sensor to determine relative changes in the fluid velocity, or measures the velocity by means of the Doppler effect. The flow is used for determining the position of the pulmonary veins orifice. Constant current anemometry is used, with the issues mentioned already above.

WO 03/086520 A1 is similar to the preceding document but measures the blood turbulence instead of velocity. The sensor used is a doppler probe that can be configured to measure the blood flow in 2D.

US 2012/0316419 A1 discloses a catheter for measuring different parameters, among others also the blood's velocity. The sensors used are at least two anemometric probes for mapping the hemodynamic parameters spatially arranged in a deployed position and configured to measure the flow velocity components in at least two different positions spaced apart in a direction orthogonal to the axial direction. The sensors are hot thin-film or hot wire probes probes, but are not specified in detail.

US 2007/0016072 A1 describes a catheter with an ultrasonic sensor tip for the measurement of blood velocity. A method is described for navigating the catheter within the human vasculature. The system is based on an ultrasound principle, and it looks mainly at the direction of the blood flow.

There is a need for an alternative way for detecting and/or locating and/or visualizing the origin of a side branch (the ostium) or the bifurcation of a vessel, without the need of using ionizing radiations and contrast dye.

It is therefore an object of the invention to create a flow sensor arrangement and method for using a flow sensor arrangement of the type mentioned initially, which overcomes the disadvantages mentioned above.

These objects are achieved by a flow sensor arrangement and method for using a flow sensor arrangement according to the corresponding independent claim 1.

The flow sensor arrangement is placed on or in an outer surface or at the circumference of an elongated body, for measuring the flow of a fluid. Three or more flow sensors can be arranged on the elongated body to measure the flow along different spatial directions.

It is understood that the measurement of flow along a particular direction may comprise only information on the magnitude of the flow, with the sign being unknown. The sign indicates the sense (positive or negative, relative to a reference orientation).

The device can be used as a system for measuring a flow quantity such as the velocity of a fluid or medium in a vessel, and can used in conjunction with a method for the interpretation of such quantities in such a way that a side branch or a vessel bifurcation or other features of the vessel is identified, and in particular the presence and the location of such a feature. The location can be determined relative to the device.

In particular, the device can be used as a system for measuring a physiological quantity such as blood velocity in a blood vessel, again in conjunction with an algorithm for the interpretation of those signals in such a way that a side branch or a vessel bifurcation or other features of the blood vessel can be identified.

In an embodiment, at least two of the flow sensors are arranged as sensor units, each sensor unit comprising at least two sensors that are arranged to measure the flow along, for example, substantially orthogonal spatial directions. The flow can be represented by the magnitude of the fluid's flow only, that is, without information about the sign. Given information about the angular orientations of the sensors of the unit, vector components of a flow vector can be computed. If the sensors are arranged orthogonally, then the flow values measured by the sensors correspond to vector components of the flow in a coordinate system defined by the orientation of the sensors.

In an embodiment, at least one the flow sensors comprises subsensors and a flow direction sign evaluation unit that is configured to determine from signals of the subsensors the sign of the flow. The direction sign evaluation unit can be implemented as part of a control unit. Consequently, not only the direction of the flow is known for a sensor or a sensor unit, but also the sign or sense of the flow in the direction(s) along the sensor(s).

The flow sensor can comprise a metallic resistance or thin film or thin plate or thermocouple.

In an embodiment, the subsensors of one flow sensor are wire anemometer sensors with their wires arranged in a collinear sequence, and wherein the flow direction evaluation unit is configured to determine the direction of the flow according to the measurement signals from the subsensors. This can be done in particular from a difference in flow values determined from the two subsensors, wherein the subsensor that returns the lower flow value corresponds and thereby indicates the direction in which the flow is heading.

In an embodiment, the flow sensors or the sensor units are distributed around the circumference of the elongated body. It is understood that the elongated body extends in a longitudinal direction and comprises a circumference in a circumferential direction, i.e. running around the elongated body in a direction orthogonal to the longitudinal direction.

In an embodiment, the flow sensors or the sensor units are arranged as sensor groups, each sensor group comprising at least three flow sensors or sensor units distributed around the circumference of the elongated body. At least two such sensor groups can be distributed along the longitudinal extension of the elongated body.

In an embodiment, the flow sensors or the sensor units or the sensor clusters are distributed along the longitudinal extension of the elongated body. Thereby arrays of sensors or sensor units or sensor clusters are formed.

A flow sensor arrangement according to one embodiment has at least one flow sensor which is a wire anemometer and is electrically connected to an evaluation unit. This embodiment can be realized independently of the features of the preceding embodiments. The evaluation unit is configured to determine a corrected flow measurement value by compensating for variations in the temperature of the fluid. That is, it takes into account a temperature measurement of the temperature of the fluid. This allows for more accurate measurements when the temperature of the sensors is close to the temperature of the flowing medium.

In an embodiment, the flow sensor arrangement is configured to determine corrected flow measurement values for one, two or more sensors, using a common temperature measurement of the temperature of the fluid. This reduces the number of wires between the evaluation unit and the sensor arrangement including the temperature sensor, as opposed to sensors where each sensor needs its own temperature compensation element.

In an embodiment, each evaluation unit comprises a bridge circuit, one of the branches of the bridge circuit comprising the corresponding sensor, and a controller configured to balance a bridge voltage, by driving to zero a controller input difference, the controller further being configured to compute the controller input difference by adding an additive correction value to a bridge voltage difference between midpoint voltages of the bridge, and to compute the additive correction value as a function of the temperature of the fluid.

A sensor typically comprises a metallic resistance or thin film or thin plate or thermocouple. The sensor is heated by resistive heating such that its temperature is raised above the fluid's temperature, and the power dissipated by conduction, convection or radiation is measured. The radiation and conduction components are negligible with respect to the convection, so the power dissipated is proportional to the fluid's flow. This technology is commonly called hot wire anemometry, and with the abovementioned control scheme the basic concept is extended, resulting in a system that is perfectly or a least highly biocompatible.

The biocompatibility is achieved because the control scheme keeps constant not the temperature, as in normal hot wire anemometry, but the temperature difference between the sensor and the blood. The sensor is heated up to a temperature that is a given difference, such as 4.5 degrees Celsius, above the blood's temperature. This limit has been proven safe with respect to the hemolysis (rupture of blood cells) and embolization (blood outgassing). In this way the blood flow measurement can be considered biocompatible.

The method for using the flow sensor arrangement as described comprises the steps of:
  measuring measurement values for at least one of the following types of measurements
    a flow velocity magnitude measured at different locations, and
    a velocity vector or velocity vector components measured at different locations, and
    a spatial gradient calculated between two or more sensors
  computing and/or creating a visual display of differences between measurement values, that is between, respectively flow velocity magnitudes, velocity vectors, velocity vector components, and spatial gradients.

In each case, measuring at different locations can be achieved by measuring with multiple different sensors or sensor units located at different locations, and/or by moving a sensor or sensor unit to such different locations and measuring at different times.

Typically, the differences are computed from measurement values obtained from spatially close or adjacent sensors or sensor units.

In an embodiment, the method comprises the steps of computing, from measurement values, difference values, and indicating the presence of a spatial flow feature if the difference values exceed a threshold, wherein in particular a spatial flow feature is a side branch or a bifurcation in a vessel. It is thus not necessary to compute and process absolute values, the difference values are a good indicator for such flow features. Also, if the differences between vector components, even without sign, are computed between different locations, changes indicate a change in flow direction or speed and therefore are also indicative of a spatial flow feature.

In an embodiment, the method comprises the steps of determining a spatial location of the spatial flow feature relative to the sensor arrangement, in particular by determining this spatial location to lie where the measurement values or the difference values between adjacent sensors reach a maximum. The maximum can be determined to be at a point in the longitudinal direction and/or at a point around the circumference of the sensor arrangement or catheter.

Optionally, also the step is performed of displaying a visual representation of the spatial location of the spatial flow feature relative to a visual representation of the sensor arrangement or of a carrier of the sensor arrangement, such as a catheter.

In an embodiment two spatial flow features can detected, for example with each one corresponding to a local maximum of the measurement or difference values. Then a distance between the two spatial flow features can be computed from the location of the two maxima. The distance can be a distance along the longitudinal direction and/or an angular difference around the circumference of the sensor arrangement or catheter.

In an embodiment, the method comprises the step of displaying a visual representation of measurement values and/or difference values positioned relative to a visual representation of the sensor arrangement or of a carrier of the sensor arrangement, such as a catheter. This representation of values can be done by displaying visual elements with sizes or coloring depending on the magnitude of the values. It gives visual cues for locating spatial flow features and guiding a user inspecting a vessel and optionally moving the sensor arrangement.

In an embodiment, the method comprises the steps of
obtaining flow measurements from three or more flow sensors;
from the values of the flow measurements and from information about the relative spatial location of the flow sensors, determining a direction of the flow in three dimensions at one or more positions at the flow sensor arrangement.

Further embodiments are evident from the dependent patent claims. Features of the method claims may be combined with features of the device claims and vice versa.

The subject matter of the invention will be explained in more detail in the following text with reference to exemplary embodiments which are illustrated in the attached drawings, which show, in schematical form:

FIG. 1 a single sensor on a longitudinally extended object such as a catheter;

FIG. 2 a pair of sensors forming a sensor unit;

FIG. 3 an operating principle for determining the sign of a flow;

FIG. 4 a sensor output when the sensor moving along a vessel passes by a side branch;

FIGS. 5-9 different views of sensor clusters;

FIG. 10 electronic bridge and controller unit;

FIG. 11 representation of flow vectors;

FIG. 12-14 different sensor arrangements;

FIG. 15-20 sensor arrangements in combination with different medical devices;

FIG. 21 flow within a vessel;

FIG. 22 representation of flow measurement;

FIG. 23 flow sensor in combination with a balloon catheter; and

FIG. 24 possible representation of flow measurements in combination with a medical image.

The reference symbols used in the drawings, and their meanings, are listed in summary form in the list of reference symbols. In principle, identical parts are provided with the same reference symbols in the figures.

A device is presented for the identification of the side branches orifice or bifurcations. The device is able of measuring the a fluid's velocity in one, two, or three directions thanks to velocity sensors placed on its surface. The measured velocities are then processed by a control unit that is able to identify the level or position of the side branch with respect to the sensor and catheter. While the examples make reference to the fluid being blood and the vessels being blood vessels, the invention completely applies to fluids and to vessels in general.

The following sections describe components that can be interconnected, defining a combined system. The components are:

The catheter or similar elongated object
The sensors
The control unit
The Catheter FIGS. 12-20 show different catheters or sections thereof. The catheter can be a long thin tube with one or multiple lumen used for the injections of drugs or other fluids (FIG. 17). It can be a special catheter used for the delivery of devices such as stent, stent grafts or stent valves (FIG. 15). It can be a guide wire (FIG. 16). It can be a balloon catheter, i.e. a catheter with at its extremity a balloon (FIG. 23). It can be a device for making a treatment with the human body, e.g. radio frequency ablation (FIG. 18). It can be a lung thin tube with some smaller catheter attached at its extremities (FIG. 19). It can be a catheter used for the cannulation with a bent extremity (FIG. 20). In general, the sensors presented herein can be used with any type of catheter including, but not limited to, a guiding catheter, diagnostic catheter, delivery catheter or a guidewire.

The Sensors

The state of the art for blood velocity measurements uses measurements based on the Doppler effect of ultrasound waves generated by piezoelectric crystals. This technology is sensitive to only one direction of the flow, and the crystal should be aligned with the blood flow. It is very complex leading to very high production costs. The technology disclosed here has far lower production costs, superior performance being less dependent on the blood flow direction, and still provides a basis for making nondestructive and safe blood flow measurements.

On the catheter's surface are placed the sensors—There can be several sensors arranged on the shaft of the catheter. In an embodiment, four sensors are placed around the circumference of the catheter. These four sensors constitute a sensor unit. Sensor units can also be constituted by two or three or more sensors. Such units of sensors can be repeated, for example, three times to five times or more along the catheter length.

In at least some embodiments, the operation of the sensors differs from classic hot wire anemometry scheme, for example, in that:
sensors can be configured to determine the direction of the fluid flow, and also of its sense. The term "direction" is understood to stand for the angular orientation of the flow and also, more general, of a vector, without information on the sign of the vector or the sense of the flow. That is, two antiparallel vectors have the same direction but opposite signs. The "sense" corresponds to the sign (positive or negative).
a temperature compensation can be implemented that allows to use a single temperature measurement for a plurality of flow sensors in order to compensate for deviations of the fluid's temperature from a reference temperature.
a temperature controller keeps a difference between the temperature of the sensor and the temperature of the fluid constant.

A sensor's configuration allows to identify the fluid's direction and sense. The direction can be identified by placing two sensors one orthogonal to the other. Supposing that the sensor has a sensing surface:

$$S=a*b$$

where a and b are two spatial dimensions of the sensor, then
IF a>>b then the sensor will be much more sensitive to the velocity orthogonal to a.

Placing two such sensors one orthogonal to the other, we will have a sensor unit able to measure the velocity in two directions. Adding a third sensor orthogonal to the previous two we can measure the velocity along the three directions.

FIG. 1 schematically shows a single sensor S1 with dimensions a and b arranged on an object C1 such as a catheter. The sensor S1 is more sensitive to one component of the flow V1, the one perpendicular to the dimension a. The dimension a is much bigger than b, in this way the sensitivity to the flow perpendicular to b (and V1) is close to zero.

FIG. 2 schematically shows the arrangement of two similar or essentially identical sensors S2, S3 one perpendicular to the other one, results in a sensor unit that can measure two separate flow components V3, V4. Placing two such units on two at least approximately perpendicular surface sections results in the sensitivity of the sensor in the three dimensional space, i.e. able to measure three separate flow components that can be essentially orthogonal.

The sense corresponding to the sign can be identified by placing two sensors one subsequent to the other and looking how one sensor influences the other. The fluid passing over a sensor will be slightly warmed up, this means that the immediately adjacent sensor will exchange temperature with a fluid that is warmer, meaning that the power dissipated by this second one will be less than without this effect. Comparing the power P1 and P2, respectively, dissipated by the two sensors, i.e. measuring the system output P1 and P2, the result is that:

IF P1>P2 THEN the sense goes from 1 to 2.
IF P1<P2 THEN the sense goes from 2 to 1.

Such a combination of sensors shall be considered to be a sensor comprising subsensors.

FIG. 3 explains this in further detail: Sensors sensitive to the flow direction can be realized by placing two subsensors S4, S5 beside one another. When the medium or fluid of the flow V5 comes in contact with the first subsensor S4, the temperature T of the medium V7 will rise and will be higher when it enters in contact with the second subsensor S5 that follows in the first subsensor when seen along the direction of the flow V5. This means that the exchanged heat power Qdot decreases V6) along the direction of the flow, and the heat power exchanged between the second subsensor S5 and the fluid will be less than the one exchanged between the first subsensor S4 and the fluid. In consequence the flow as observed or measured will be lower in the second subsensor S5 when compared to the first subsensor S4. Comparing the two measured quantities, the result is that if the fluid flows from the first S4 to the second subsensor S5 the output voltage is higher in the first S4 and lower in the second subsensor S5, and conversely when the output voltage is higher in the second subsensor S5 and lower in the first subsensor S4 the fluid flows from the second S5 to the first subsensor S4.

FIG. 4 shows measurements of flow magnitude A1 (vertical axis) at different positions within the aorta A2 (horizontal axis), including positions in front of side branches, where an increase in flow magnitude is evident.

FIG. 5 shows a single sensor configuration. A sensor cluster or group comprising different single sensors S6, S7, S8 is arranged on the catheter C1, the single sensors, for example, distributed around its circumference. The cluster can measure the velocity magnitude at different locations around the catheter, as described in FIG. 1.

FIG. 6 shows two sensors configuration. A sensor cluster or group comprising different sensor units or couples S12-S13 or S10-S11 is arranged on the catheter C2, the sensor units, for example, distributed around its circumference. A single sensor unit or couple can measure the flow in two directions as described in FIG. 2. When the units of the cluster are placed around the circumference of the catheter, three dimensional information in the flow can be measured.

The arrangement of FIG. 6 can also be realised with sensors having subsensors, thus measuring also the sense of the direction.

FIG. 7 shows a four sensor configuration. A cluster comprising six sensors in three sensor units is shown. Each sensor S14, S15, S16, S17, S18. S19 is able to measure the magnitude and sense of the flow, since they exhibit the configuration with subsensors as explained in FIG. 3. A single unit comprising a pair of orthogonally arranged sensors is able to measure the flow magnitude in two directions, and also the sense. The flow in the whole three dimensional space can be measured placing different sensors around the catheter C3. The arrangement of FIG. 7 can also be realised with sensors without subsensors, i.e. for measuring only the direction but not the sense.

In some embodiments, the sensors are placed along the catheter shaft and around the catheter. FIG. 8 shows three sensors placed around the circumference of the catheter C4. Three sensors S23, S24, S25 are aligned with or extend along the catheter's circumference and the other three sensors S20, S21, S22 are aligned longitudinally with respect to the catheter (or orthogonally to the first three sensors S23, S24, S25 or the circumference) in order to realize three configurations such as in FIG. 2.

FIG. 9 shows four sensors placed around the circumference of the catheter C7. Four sensors S30, S31, S32, S33 are aligned with or extend along the catheter's circumference and the other four S26, S27, S28, S29 are aligned longitudinally with respect to the catheter (or orthogonally to the first four sensors S30, S31, S32, S33 or the circumference) in order to realize four configurations such as in FIG. 2.

FIGS. 8 and 9 can also be considered to show sectional views of arrangements as in FIGS. 5 to 7 at different positions along the length of the respective catheter.

FIG. 10 shows a measurement arrangement with a measurement bridge with a first bridge leg with resistances R2, R3 and a second bridge leg with a resistance R1 and the RTD sensor S34. The voltages at the midpoints of the two bridge legs serve as bridge voltage inputs I2, I3 to a microcontroller D1. The temperature of the sensor is kept constant by measuring the difference between the two inputs I2, I3. The difference is then input to a controller. This can be, for example, a proportional, integrative, differential (PID) controller, or a PI or PD or P controller. The controller closes the control loop by adapting an output signal O1 or output voltage driving the measurement bridge R1, R2, R3, S34. The controller can be implemented by analog or digital signal or data processing means or can be implemented in firmware or another program of the microcontroller D1. The (micro)controller can also comprise a compensation for the fluid's temperature $T_f$ measured by the sensor T1 and given as further input I1 to the (micro)controller. The output O1 is proportional to the magnitude of the fluid flow on the sensor's S34 surface.

Hot wire anemometry sensors generally depend on the fluid's temperature. This temperature is usually assumed to be constant, or the temperature differences between sensor and fluid are so high (100-200° C., e.g.) that the temperature difference between the sensor and the fluid can be considered as constant. In the present case, due to physiological constraints, the temperature gap cannot be too high, so possible fluctuations in the fluid's temperature must be compensated for. The disclosed system compensates for temperature fluctuations with a correction factor that multiplies the sensor's output. The correction factor c has the form:

$$c = \frac{R_{S0} + R_0 * \alpha * \Delta T}{R_1 + R_{S0} + R_0 * \alpha * \Delta T} - \frac{R_{S0}}{R_1 + R_{S0}}$$

Where:
$R_{S0}$=resistance of the RTD used at a nominal temperature $T_n$, for example $T_n$=41.5° C.
$\Delta T = T_f - T_n$; Fluid's temperature $T_f$ variation from the nominal fluid temperature $T_n$
$\alpha$=sensor's temperature coefficient of resistance
$R_1$=bridge resistance in the same bridge leg as the measurement resistor or RTD, in a bridge circuit as in FIG. 10.

The correction factor c is multiplied with the output value O1 of the control unit D1 giving an additive correction value $\Delta V$:

$$\Delta V = c*O1$$

The additive correction value $\Delta V$ is added to the difference of the two inputs I2, I3, and the result is then used as input to, for example, a PID controller:

$$\text{PID input} = I2 - I3 + \Delta V$$

or to another controller that drives its input value to zero. The PID algorithm can be implemented as follows:
Proportional part: multiplying the measurement with a proportional gain Kp
Integrational part: summing up the PID input every iteration and multiply the sum with an integrator gain Ki $$esum = esum + (\text{PID input} * dt)$$

Derivation part: subtracting the PID input of the last iteration (n−1) from the actual PID input and multiplying with a differentiator gain Kd $$\text{derivation} = \text{PID input }(n-1) - \text{PID input}/dt$$

Adding the 3 parts together:

$$\text{output }(O1) = Kp*\text{PID input} + Ki*esum + Kd*\text{derivation}$$

The PID controller can include some kind of saturation filter to avoid integration windup and DA-Converter overflow.

The result (regardless of whether a PID controller of other controller is used) is that the controller using the correction factor as described causes the temperature of the sensor to follow the temperature of the fluid with a temperature offset. If the temperature of the fluid deviates from its nominal temperature $T_n$ the correction factor causes he bridge with the control loop to drive the sensor temperature to deviate from the nominal sensor temperature by the same difference. In other words, the correction factor and additive correction factor, given the fluid temperature, change the reference voltage to which the midpoint of the measurement leg of the bridge is driven, and correspondingly also changes the temperature to which the sensor is driven.

The abovedescribed temperature measurement scheme allows for the compensation for variations of the temperature of the fluid or medium. Since the temperature sensor T1 is not part of the bridge circuit, a single temperature sensor T1 can be used for the compensation in a plurality of flow sensors or a plurality of associated measurement bridge circuits, respectively. Effectively, the temperature compensation has been moved from the bridge into the control unit D1, and thus can be performed for all sensors based on the same temperature reading.

The Control Unit

The control unit CU processes the signals coming from the different sensors and can display the measurements and/or information on the location of vessel features such as the side branches or bifurcations. In the simplest case, the information the location of such features is displayed or output in relation to the catheter, that is, with an indication at where the feature lies with along the length of the catheter, and/or at what location along the circumference.

With respect to the state of the art that uses complex sensor configurations, the method described here can identify the position of side branches and other features of a vessel from very simple measurements. Different sensor configurations are presented here, the basic configuration uses only one sensor unit and a more complex example uses four sensors.

The location of a side branch orifice or bifurcation is characterized by a change in velocity magnitude, and/or change in velocity direction. This the present invention compares the signal acquired from different sensors placed on the catheter's shaft, and/or different measurements acquired by one sensor in different time instants in different ways in order to identify the side branches and bifurcations. The comparison can be made through one of or a combination of measurements of difference in the velocity magnitude, difference in the velocity vector, and changes in the spatial gradient calculated between two or more sensors:

Difference in the velocity magnitude acquired by at least one sensor unit with two or more sensors:

At least two velocity magnitudes are measured $v_1$ and $v_2$ (by two different sensors or by one sensor at two different points in time) placed along the catheter, e.g. the sensors can be in the configuration shown in FIG. 5, and could also be essentially any pair of sensors from the configuration represented in FIG. 12. In this FIG. 12 an array S35 of sensors as described in FIG. 5 is placed on the catheter body C9. The two sensors are preferably oriented in the same direction.

The two measurements $v_1$ and $v_2$ which are scalar values, are then subtracted:

$$v_1 - v_2$$

The velocity measured by the sensor in proximity of the side branch (or bifurcations) will be higher than the one further away from the side branch, the peak in FIG. 4 characterizes the flow in front of a side branch. So should the difference be positive then the sensor n.1 is inferred to be more close to the side branch orifice. Should the difference be negative then will be the sensor n.2 is detected to be closer to the side branch's orifice. Should the difference be non-relevant, i.e. have an absolute value that is smaller than a threshold, then the both sensors will be either in similar proximity of a side branch or far from such a feature. In this case the position of the side branch, if there is one, can still be identified by looking at the difference of another pair of measurements.

Difference in the velocity vector acquired by at least one sensor unit with two or more sensors:

In case the velocity is measured by a sensor setup as represented in FIG. 6, then the velocity magnitude and its direction in the sensor's plane can be identified. In this case the difference of the two components of two different measurements made by any pair of two sensor units (FIG. 6) from e.g. the configuration of FIG. 13 can be computed $$\overline{v_1} - \overline{v_2}, \text{ or } (v_{1x} - v_{2x}, v_{1y} - v_{2y})$$

$$(v_{1x} - v_{1y}, v_{2x} - v_{2y})$$

The identification of the side branches can be based on comparing the velocity magnitude, as already explained in the method above. But the identification can be made more robust if also the flow direction is taken into account, even if the sign or sense is not known. In particular, this can be done by comparing the x component with the y component, within a single sensor unit or between two or more sensor units. When one measurement is much bigger than the other we can conclude that the flow has changed direction, which indicates the presence of a side branch or a bifurcation.

Changes in the spatial gradient, where the gradient is calculated between two or more sensors:

In this case the sensor unit is organized as represented in FIG. 7, and several sensor units are displaced along the catheter as represented in FIG. 14. In this case the full velocity vector can be characterized in magnitude, direction and sense. And the spatial gradient along a catheter can be defined.

$$\Delta \bar{v}$$

In this case the system can identify the position of side branches and bifurcations using the two systems defined above. But also the flow sense will be defined. In such a way the sense of the blood's stream will be also known, giving information if the catheter is advancing with or against the blood stream.

FIG. 11 shows combining the measurements made by each sensors A4, A3, A5 whereby it is possible to identify the three dimensional components of the velocity V6.

The more sensors or sensor units are placed along the elongated body or catheter, the more detailed the observations get. FIG. 13 a shows an array S36 of sensor clusters as described in FIG. 6 placed on a catheter body C10. FIG. 14 shows an array S37 of sensors clusters as described in FIG. 7 placed on the catheter body C11.

FIG. 15 shows a catheter C12 can be used to deploy devices such as stent D1, represented in the figure as semi-deployed: one can identified a portion that is expanded D1.2 and a portion that is still crimped D1.1; in the surgical procedure the stent is inserted into the vessel completely crimped on the catheter and then is expanded. The stent could be also a stent valve or a stent graft. In this case the sensors S38, S39, S40 can be either placed on the catheter's body as presented in FIGS. 12, 13, 14, for example, or on long thin wires W1 originating from the catheter and running alongside the stent D1.

Figure 22:
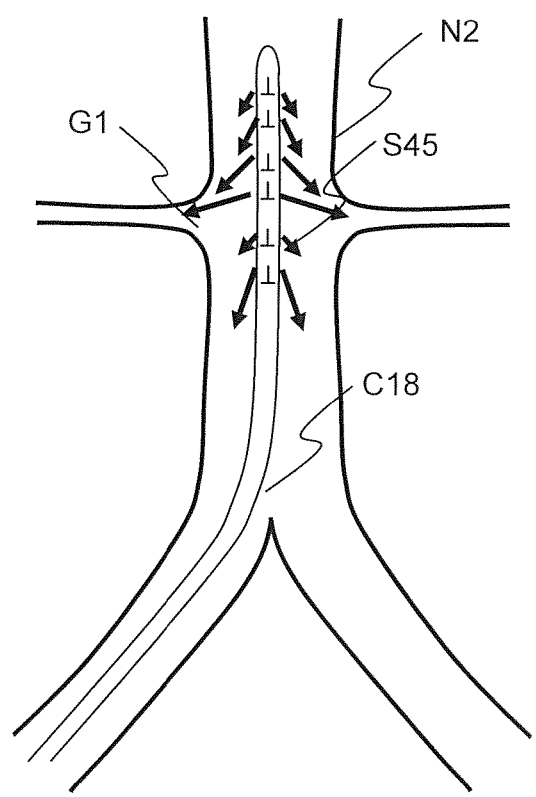

FIG. 22 shows how a system can display the direction of the flow with graphical means, e.g. arrows G1. When the flow enters in the side branch, by comparing the velocity of the sensors before and after the side branch, it is identified that the flow goes inside a branch. The direction of the arrow representing the flow direction indicates the ostium. N2 is the main vessel, C18 is an example of catheter, S45 is the sensor.

Figure 1:
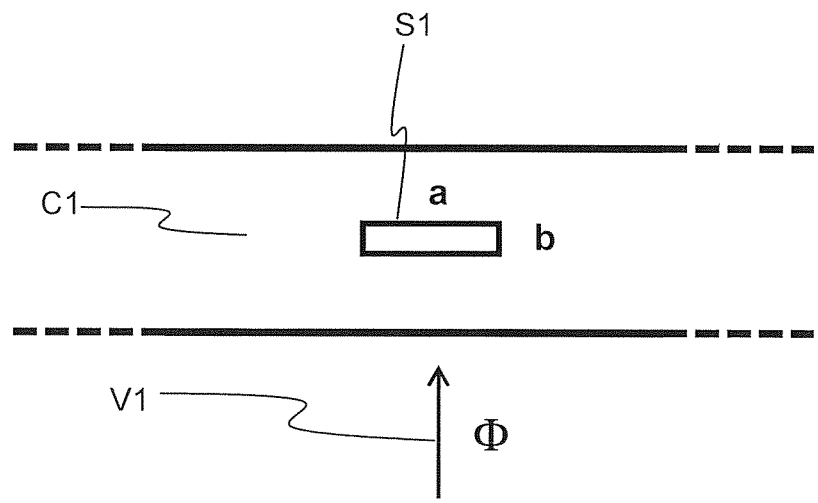
Figure 2:
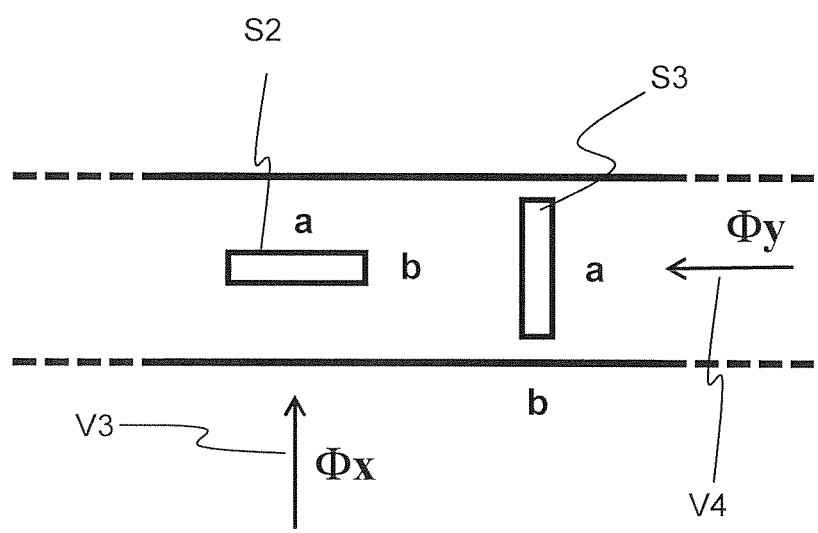
Figure 3:
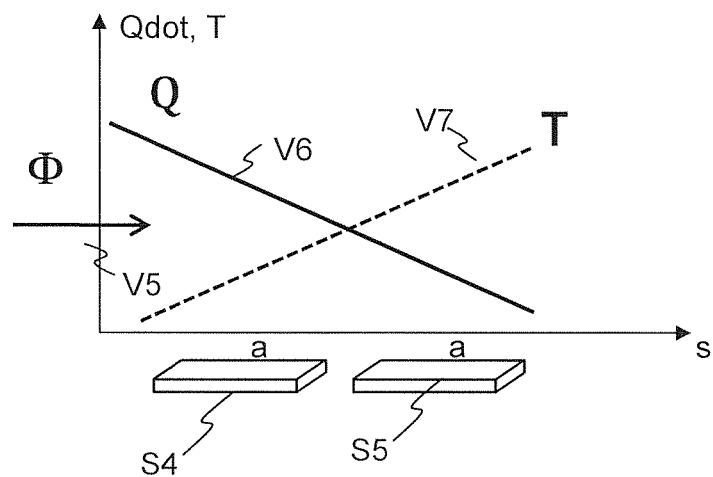
Figure 4:
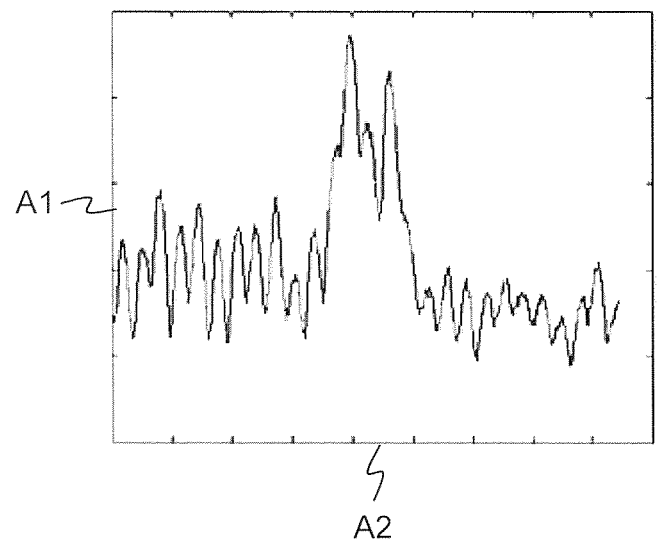
Figure 5:
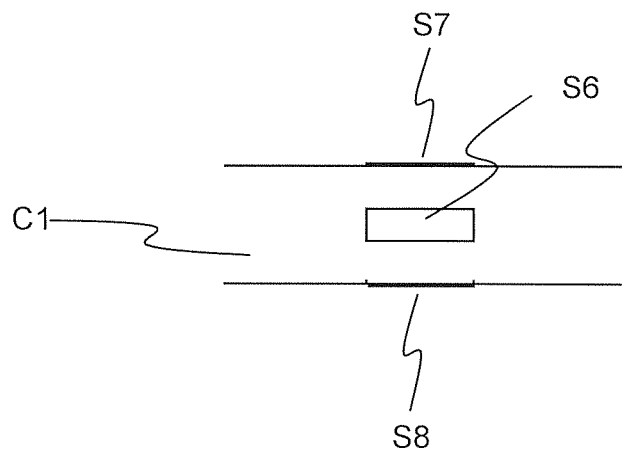
Figure 6:
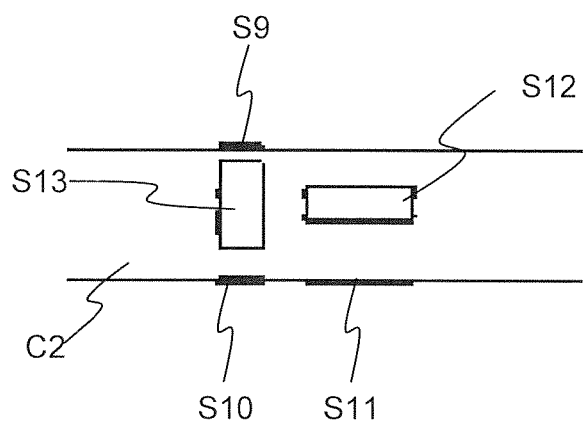
Figure 7:
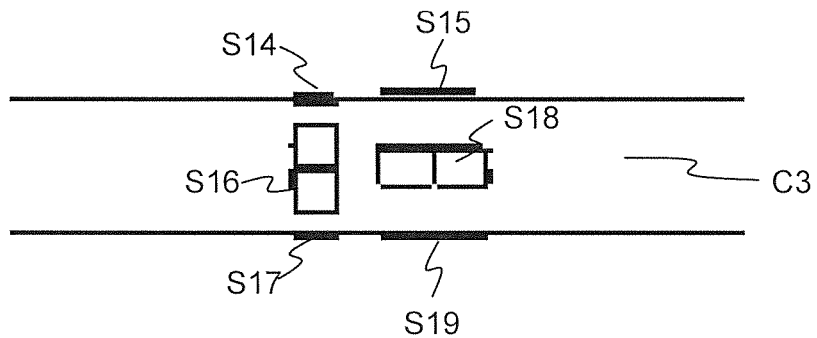
Figure 8:
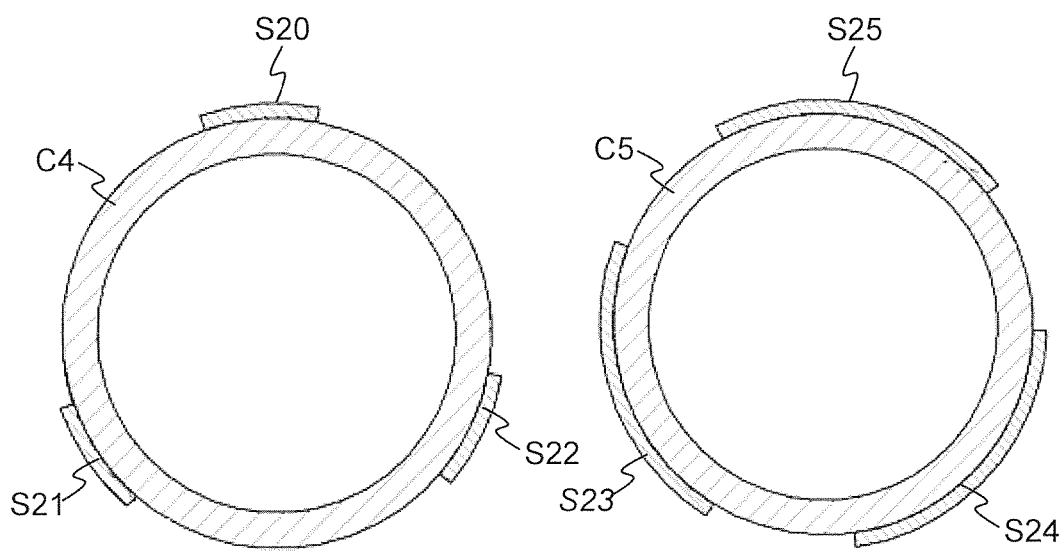
Figure 9:
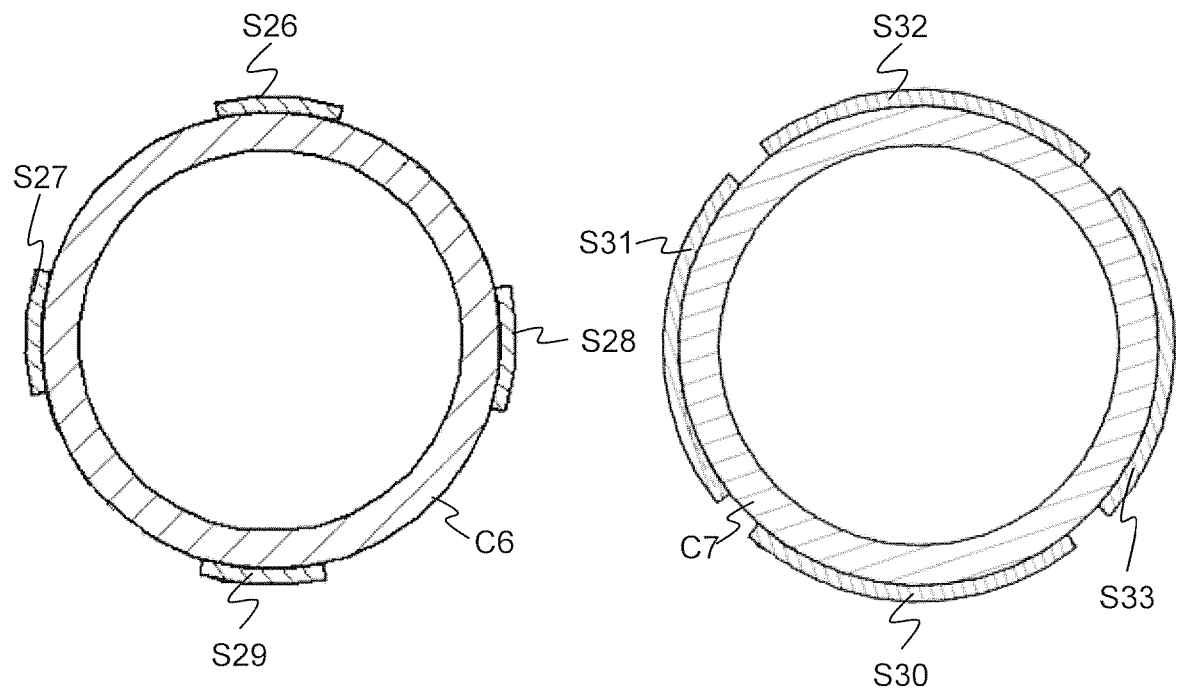
Figure 10:
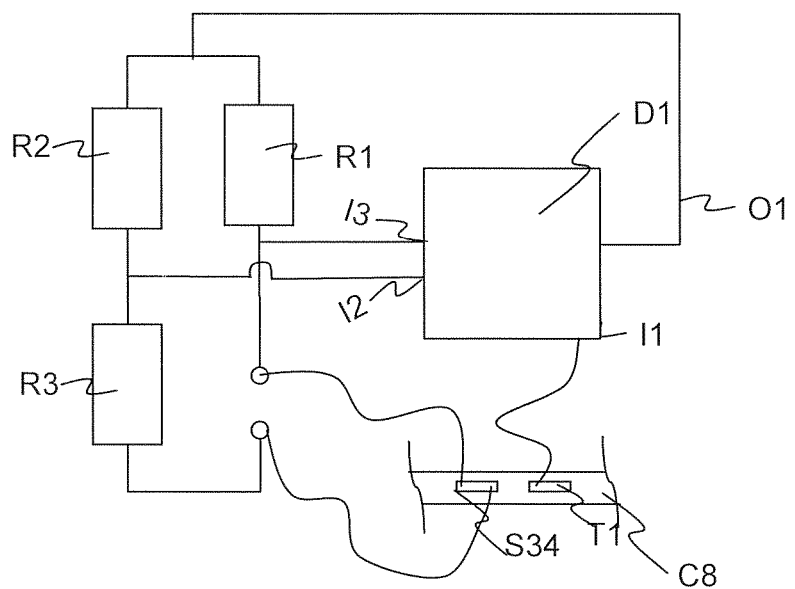
Figure 11:
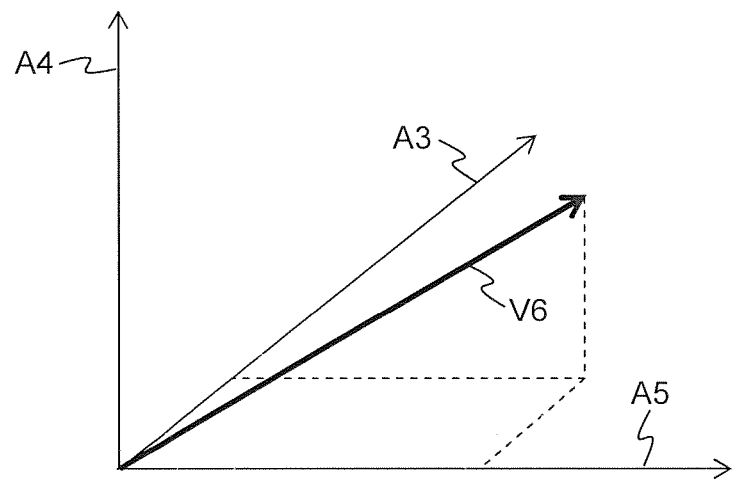
Figure 12:
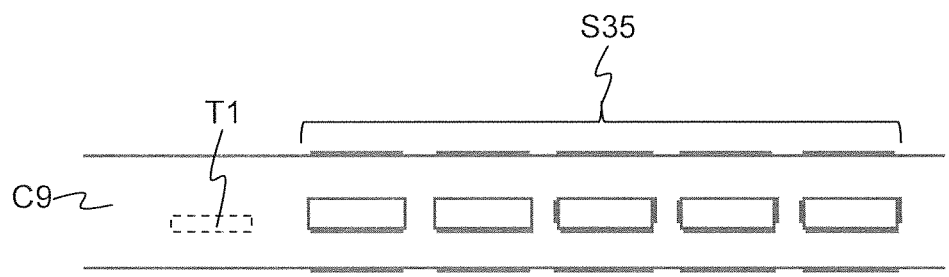
Figure 12:
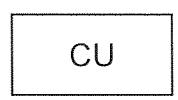
Figure 13:
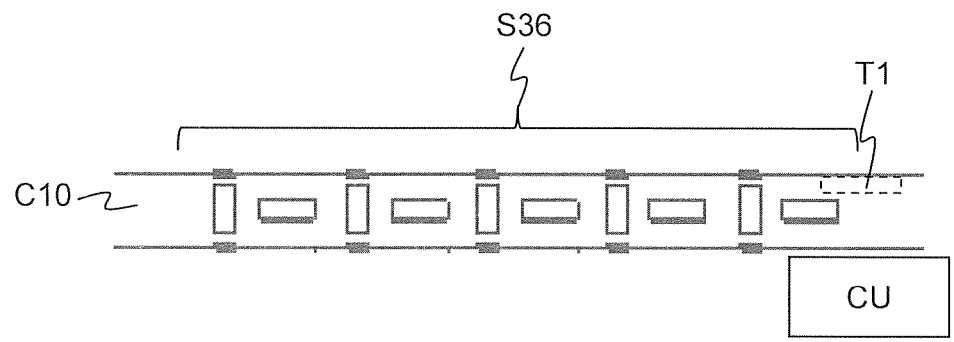
Figure 14:
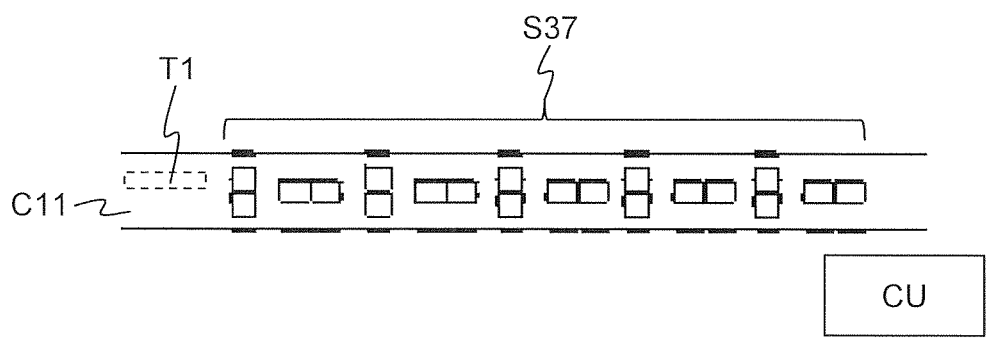
Figure 15:
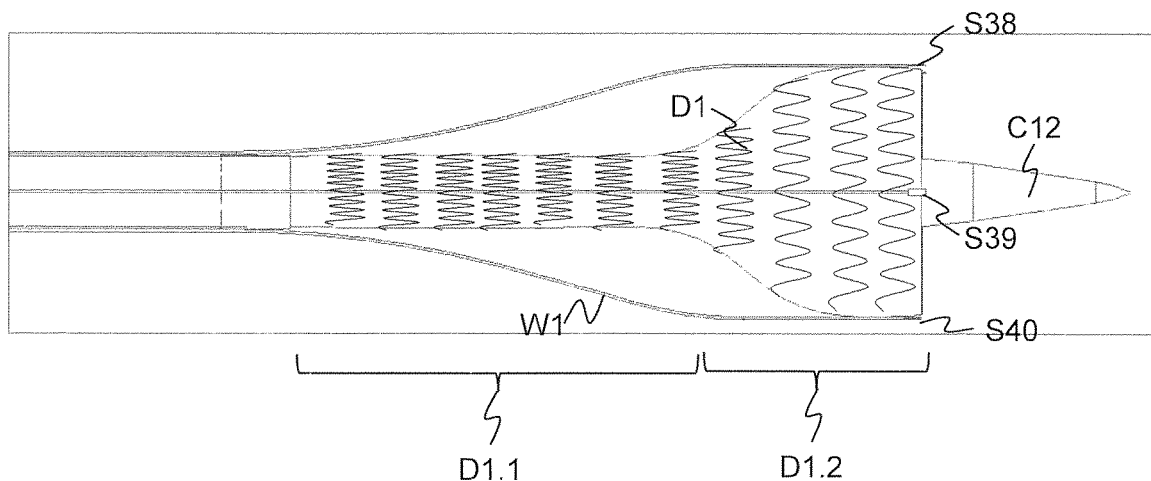
Figure 16:
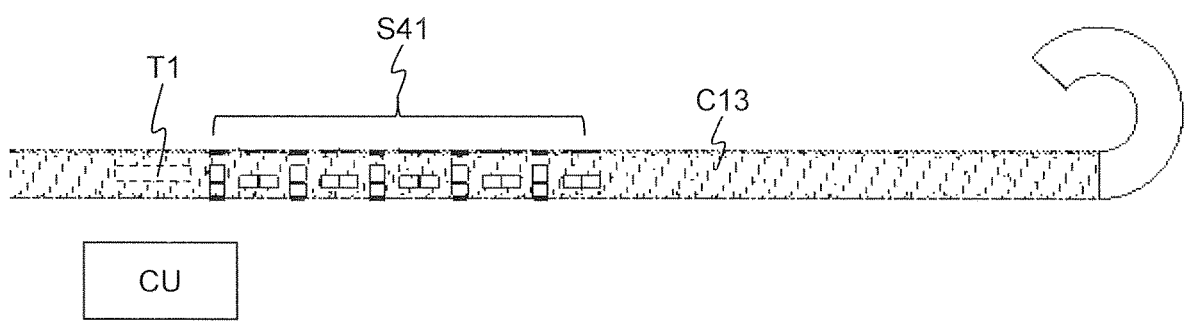
FIG. 16 shows how a sensor array S41 as described in FIGS. 12, 13, 14 can be used with a guidewire C13.
Figure 17:
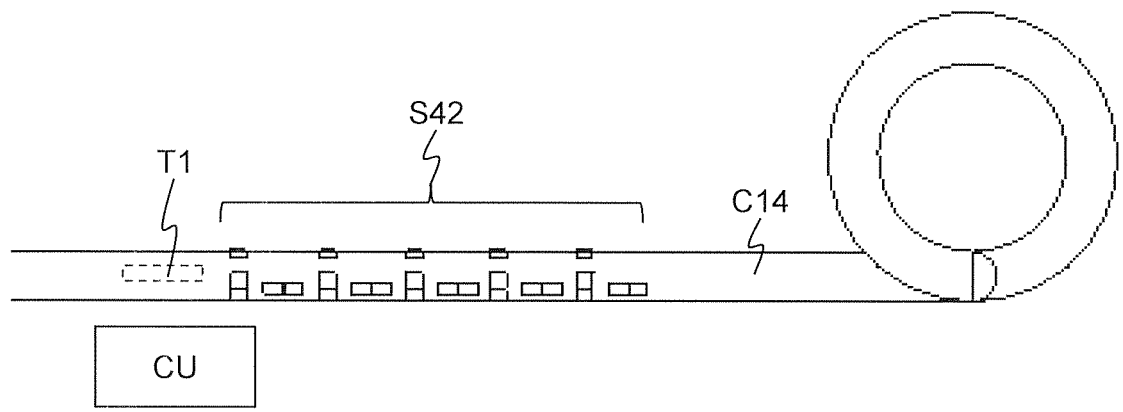
FIG. 17 shows how a sensor array S42 as described in FIGS. 12, 13, 14 can be used with a pig tail catheter C14.
Figure 18:
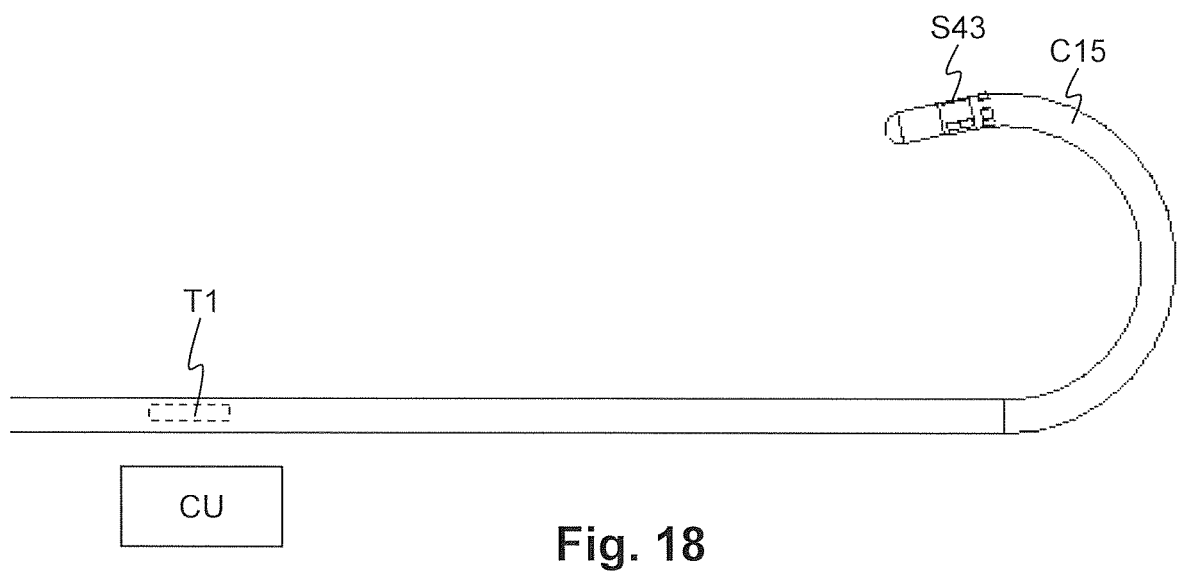
FIG. 18 shows how the sensor array as described in FIGS. 12, 13, 14 can be used with a catheter used for radiofrequency ablation or for measuring electrophysiological activity C15. The sensors, that is, at least one sensor unit or one sensor cluster, can be placed on the catheter tip S43 for identifying the position of blood vessels openings.
Figure 19:
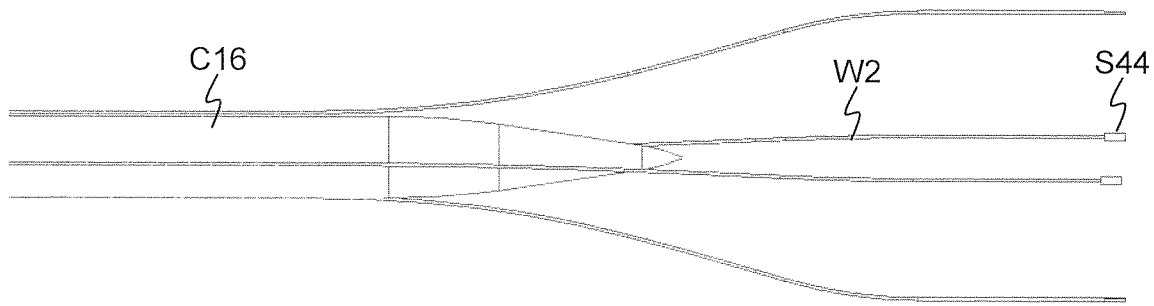
FIG. 19 shows sensors S44 placed on a main shaft of the catheter C16 and/or on small catheters W2 attached to the bigger one (FIG. 19 does not show structural elements holding the sensors in place).
Figure 20:
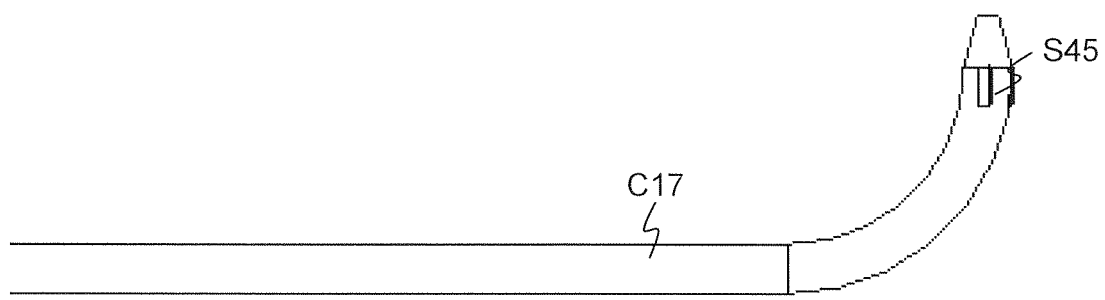
FIG. 20 shows how a sensor array as described in FIGS. 12, 13, 14 can be used with a catheter used for the cannulation of a vessel C17. The sensor can be placed on the catheter tip S45 for identifying the position of blood vessels openings.
Figure 21:
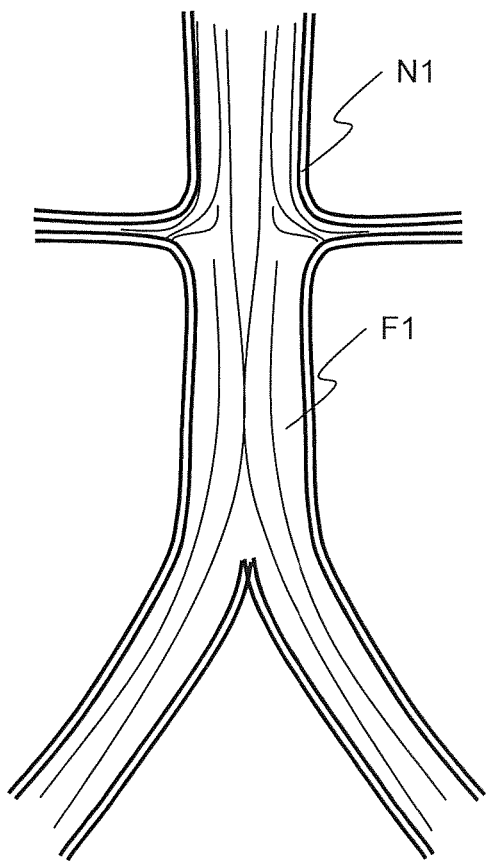
FIG. 21 shows a flow F1 into a main vessel N1.
Figure 23:
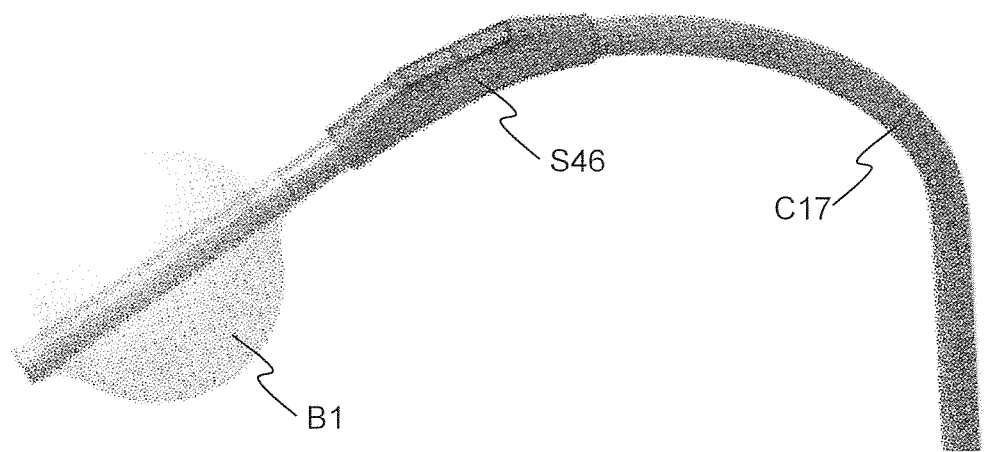

FIG. 23 shows the sensor array as described in FIGS. 12, 13, 14, used with a balloon catheter used for performing an angioplasty or occluding a vessel C17. The sensor can be placed on the catheter tip close to the balloon B1 or on the catheter shaft S46 for identifying the position of blood vessels openings.

Figure 24:
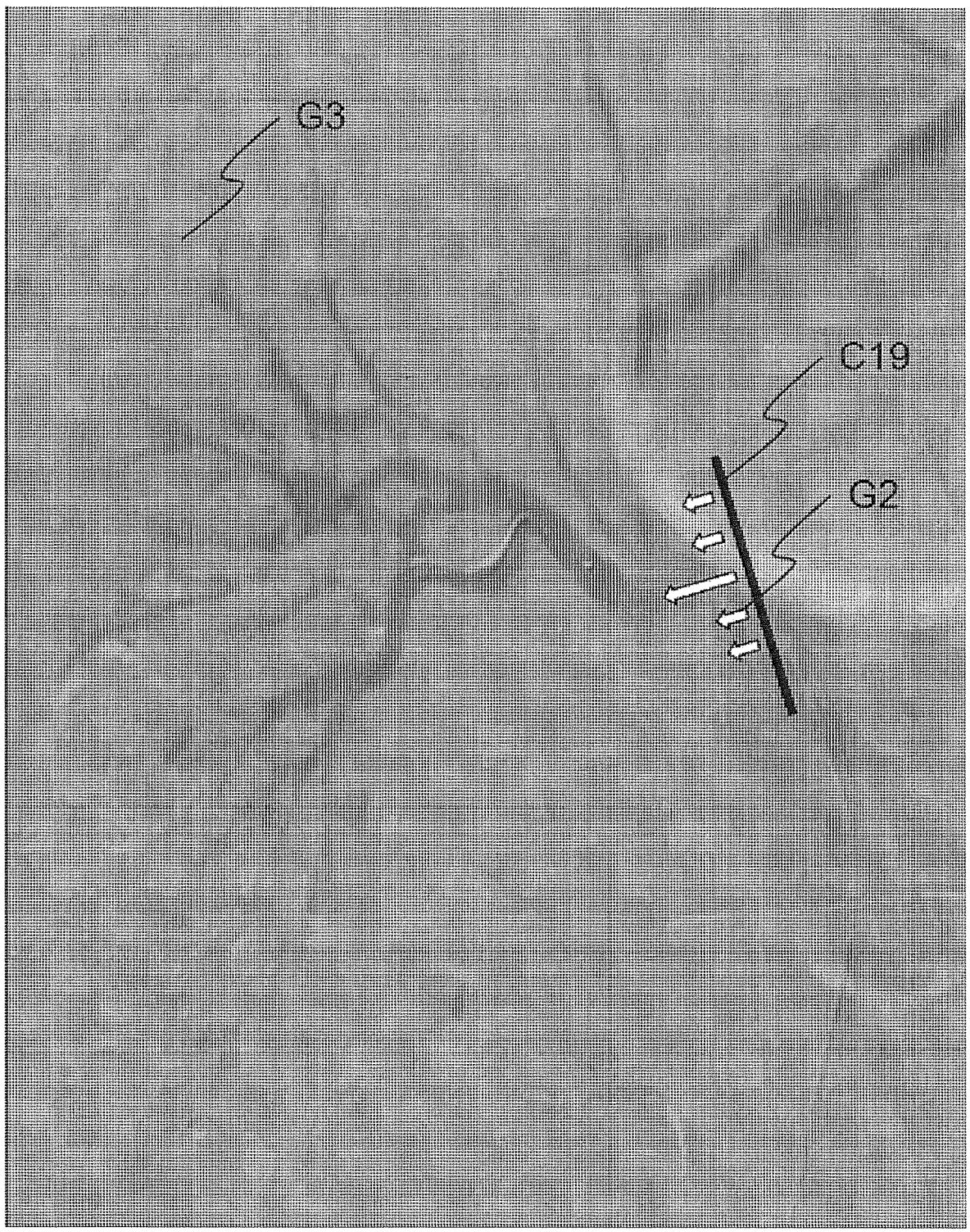

FIG. 24 The visualization of the flow information from the sensor or sensors can be represented as an augmentation of a normal fluoroscopic image (G3). A catheter position can be identified with techniques of image processing of a fluoroscopic image, and then the image can be automatically augmented by superposing an image of the catheter or sensor arrangement C19 and a graphical representation, for example, arrows representing a fluid or blood flow G2. Alternatively, bars can be displayed without arrows, indicating magnitude of the flow but not the sense of the flow. Alternatively, other graphical elements can be displayed alongside the representation of the catheter, indicating the magnitude of the flow by, for example, their size and/or their color. Such other elements can be circles. The example of FIG. 24 shows with the longest arrow a maximum value, which therefore is indicative of a spatial flow feature, in the present case a side branch. The location of the arrow (or other graphical element) representing the maximum value indicates the location of the spatial flow feature relative to the sensor arrangement or catheter, and thus also in the correct spatial relation to the fluoroscopic image. In other embodiments (not shown) the measurement (or difference) values and corresponding maximum values are evaluated around the circumference of the sensor arrangement and optionally also displayed, for example in a sectional view of the the sensor arrangement and vessel, in a section plane normal to the longitudinal axis of the sensor arrangement, or in a 3D representation. The angular location of a side branch or other spatial flow feature is indicated at a circumferential location where a measurement value or a difference value exceeds a threshold or reaches maximum.

Further applications of the sensors, units and clusters or groups described:

Measurement of the endoleaks within a stented vessels. The sensor left in place after the stent implantation can be used for identifying paravalvular leaks (TAVI valve) and endoleaks in the EVAR.

The sensors could be wireless and left in place in the anatomy attached to the device.

The sensing system can be coupled with a tracking device that is able to track the 3D position of the sensor in space, thereby creating a flow map in two or three dimensions.

While the invention has been described in present embodiments, it is distinctly understood that the invention is not limited thereto, but may be otherwise variously embodied and practised within the scope of the claims.

The invention claimed is:

1. An apparatus comprising:
   an elongated structure extending in a longitudinal direction;
   at least two spatially adjacent flow sensors arranged as a sensor unit to measure a flow or a fluid along substantially orthogonal directions, each of the at least two flow sensors being configured to measure a quantity of the flow of the fluid, wherein each of the at least two flow sensors has a corresponding, respective sensing surface having a first spatial dimension which is larger than a second spatial dimension of the sensing surface, wherein each of the at least two flow sensors is more sensitive for measuring the flow of the fluid orthogonal to the first spatial dimension than parallel to the first spatial dimension and wherein the sensing surfaces of the at least two flow sensors are arranged substantially orthogonal to each other and arranged subsequent to one another in a direction in which the flow of fluid is measured, said at least two spatially adjacent flow sensors being mounted on said elongated structure, the at least two spatially adjacent flow sensors including a first flow sensor and a second flow sensor, the first flow sensor being longer in said longitudinal direction and extending parallel to said longitudinal direction, the second flow sensor being longer in a direction which extends perpendicular to the longitudinal direction than the second flow sensor is in the longitudinal direction; and a microcontroller configured to determine, from the measured quantity of flow of the fluid, at least one of: a velocity of the flow of the fluid, one or more components of a velocity vector of the flow of the fluid, an angular orientation of the flow of the fluid and a sign of the flow of the fluid.

2. The flow sensor arrangement of claim 1, wherein the flow sensor of the at least two flow sensors that returns a lower flow value corresponds to the direction in which the flow is heading.

3. The flow sensor arrangement of claim 1, wherein the microcontroller is further configured to control the temperature of the one or more flow sensors and configured to determine a corrected quantity of the flow of the fluid by taking into account a measurement of the temperature of the fluid, wherein the microcontroller is configured to keep a temperature difference between the one or more flow sensors and the fluid constant.

4. The flow sensor arrangement of claim 3, wherein the microcontroller is configured to determine the corrected quantity of the flow of the fluid based on a correction factor that is dependent on a resistance of a resistance temperature detector at a nominal temperature and on a difference between the measured temperature of the fluid and the nominal temperature.

5. The flow sensor arrangement of claim 4, further comprising a bridge circuit comprising a plurality of branches, wherein each one of said branches comprises a corresponding one of said flow sensors, and wherein the microcontroller is configured to balance a bridge voltage for determining the corrected quantity of the flow of the fluid.

6. The flow sensor arrangement of claim 1, wherein the one or more flow sensors: i) are moveable between two or more different locations and ii) measure, at each of two or more different locations, at least one of:
 a velocity magnitude of the flow of the fluid;
 a velocity vector or velocity vector components of the flow of the fluid; and
 a spatial gradient of the flow of the fluid.

7. A catheter comprising:
an elongated body extending in a longitudinal direction; and a flow sensor arrangement comprising:
at least two spatially adjacent flow sensors arranged as a sensor unit to measure a flow or a fluid along substantially orthogonal directions, each of the at least two flow sensors being configured to measure a quantity of the flow of the fluid, wherein each of the at least two flow sensors has a corresponding, respective sensing surface having a first spatial dimension which is larger than a second spatial dimension of the sensing surface, wherein each of the one or more flow sensors is more sensitive for measuring the flow of the fluid orthogonal to the first spatial dimension than parallel to the first spatial dimension and wherein the sensing surfaces of the at least two flow-sensors are arranged substantially orthogonal to each other and arranged subsequent to one another in a direction in which the flow of fluid is measured, said at least two spatially adjacent flow sensors being mounted on said elongated structure, the at least two spatially adjacent flow sensors including a first flow sensor and a second flow sensor, the first flow sensor being longer in said longitudinal direction and extending parallel to said longitudinal direction, the second flow sensor being longer in a direction which extends perpendicular to the longitudinal direction than the second flow sensor is in the longitudinal direction; and a microcontroller configured to determine, from the measured quantity of flow of the fluid, at least one of a velocity of the flow of the fluid, one or more components of a velocity vector of the flow of the fluid, an angular orientation of the flow of the fluid and a sign of the flow of the fluid.

8. The catheter of claim 7, wherein the at least two of said spatially adjacent flow sensors are distributed around the circumference of the elongated body.

9. The catheter of claim 7, wherein the at least two of said spatially adjacent flow sensors are distributed on an inner surface of the elongated body.

10. The catheter of claim 7, wherein the at least two spatially adjacent flow sensors is arranged as part of a first sensor group the first sensor group comprising at least three flow sensors distributed around the circumference of the elongated body, the catheter further including a second sensor group, the first and second sensor groups being distributed along a longitudinal extension of the elongated body.

11. The catheter of claim 7, wherein the microcontroller is configured to determine information about a vessel into which the catheter is inserted based on a change of at least one of: the measured velocity of the flow of the fluid, the one or more components of the velocity vector of the flow of the fluid, the angular orientation of the flow of the fluid and the sign of the flow of the fluid.

12. The catheter of claim 11, wherein the information about the vessel is the presence of a side branch or bifurcation of the vessel, wherein the at least two of said flow sensors are configured and arranged to measure the quantity of the flow of the fluid at two or more different locations in the vessel.

13. The catheter of claim 7, wherein said first and second sensors form a sensor pair that extends in the longitudinal direction with the second sensor being arranged on the elongated body of the catheter behind the first sensor.

14. The catheter of claim 7, wherein the elongated body of the catheter is a tube which extends in said longitudinal direction.

15. A method of determining the presence of a side branch or bifurcation of a vessel, the method comprising:

inserting a catheter into the vessel, the catheter comprising a flow sensor arrangement including at least two spatially adjacent flow sensors, arranged as a sensor unit to measure a flow or a fluid along substantially orthogonal directions, each of the at least two flow sensors being configured to measure a quantity of the flow of the fluid, wherein each of the at least two flow sensors has a corresponding, respective sensing surface having a first spatial dimension which is larger than a second spatial dimension of the sensing surface, wherein each of the at least two flow sensors is more sensitive for measuring the flow of the fluid orthogonal to the first spatial dimension than parallel to the first spatial dimension and wherein the sensing surfaces of the at least two flow sensors are arranged substantially orthogonal to each other and arranged subsequent to one another in a direction in which the flow of fluid is measured, the at least two spatially adjacent flow sensors being mounted on said elongated body and including a first flow sensor and a second flow sensor, the first flow sensor being longer in said longitudinal direction and extending parallel to said longitudinal direction, the second flow sensor being longer in a direction which extends perpendicular to the longitudinal direction than the second flow sensor is in the longitudinal direction;

measuring the velocity of the flow of the fluid in the vessel at a first position;

moving the catheter and measuring the velocity of the flow of the fluid in the vessel at a second position; and determining the presence of the side branch or bifurcation of the vessel by comparing the velocity of the flow of the fluid in the vessel at the first position and the velocity of the flow of the fluid in the vessel at the second position.

16. The method of claim 15, wherein the step of determining comprises determining the location of the side branch or bifurcation of the vessel by comparing the velocity of the flow of the fluid in the vessel at the first position and the velocity of the flow of the fluid in the vessel at the second position.

17. The method of claim 15, wherein the method further comprises:

controlling the temperature of the flow sensor to keep a temperature difference between the flow sensor and the fluid constant; and determining a corrected quantity of the flow of the fluid by taking into account a measurement of the temperature of the fluid.

18. The method of claim 5, wherein the corrected quantity of the flow of the fluid is determined based on a correction factor that is dependent on a resistance of a resistance temperature detector at a nominal temperature and on a difference between the measured temperature of the fluid and the nominal temperature, and wherein the corrected quantity is determined based on balancing a bridge voltage in a bridge circuit comprising a branch which comprises the flow sensor.

* * * * *